United States Patent [19]

Bode

[11] Patent Number: 5,279,967
[45] Date of Patent: Jan. 18, 1994

[54] FLUORESCENT LABELING OF HYDROCARBONS FOR SOURCE IDENTIFICATION

[75] Inventor: Heinrich E. Bode, Richmond, Tex.

[73] Assignee: Nalco Chemical Company, Naperville, Ill.

[21] Appl. No.: 825,220

[22] Filed: Jan. 24, 1992

[51] Int. Cl.$^5$ ............................................. G01N 37/00
[52] U.S. Cl. ........................................ 436/56; 44/419
[58] Field of Search ............................ 436/56; 44/419

[56] References Cited

U.S. PATENT DOCUMENTS

| | | | |
|---|---|---|---|
| 3,733,178 | 5/1973 | Eriksen | 436/56 |
| 4,009,008 | 2/1977 | Orelup | 436/56 |
| 4,141,692 | 2/1979 | Keller | 44/454 |
| 4,146,604 | 3/1979 | Kleinerman | 436/800 |
| 4,278,444 | 7/1981 | Beyer et al. | 44/59 |
| 4,755,469 | 7/1988 | Showalter | 436/27 |
| 4,783,314 | 11/1988 | Hoots et al. | 422/3 |

FOREIGN PATENT DOCUMENTS 0361310 11/1931 United Kingdom ................. 436/56

*Primary Examiner*—Lyle A. Alexander
*Attorney, Agent, or Firm*—Kinzer, Plyer, Dorn, McEachran & Jambor

[57] ABSTRACT

A hydrocarbon liquid identification and tracing system based on fluorescence, high pressure liquid chromatography or thin layer chromatography and N-substituted or N,N'-dialkyl-4-amino-1,8-naphthalimides as the fluorophores is described.

The liquid fuel tracing system based on the above naphthalimides is based on the $2^n-1$ binomial system and provides inexpensive and extremely accurate and sensitive monitoring and source identification.

11 Claims, No Drawings

FLUORESCENT LABELING OF HYDROCARBONS FOR SOURCE IDENTIFICATION

FIELD OF THE INVENTION

This invention involves identification of liquid hydrocarbons using a base 2 or higher encoding system in order to establish or trace provenance. The term provenance is used in the sense of origin, form or quality of the hydrocarbon to be traced. Further, the base 2 or higher encoding system is, in this invention, using specified fluorophores which provide high analytical sensitivity and reproducibility.

BACKGROUND OF THE INVENTION

Environmental agencies are addressing "non-attainment" areas, meaning compacted metropolitan areas, i.e. the largest cities, where motor vehicle emissions have not yet attained established environmental standards. The environmental requirement is or will require that motor fuels for consumers, within a given metropolitan radius, be modified to reduce hydrocarbon emissions and achieve cleaner burning by revising the hydrocarbon distribution and by incorporation of certain oxygenates. The oxygenate addition is to improve octane rating, to produce a smoother burning fuel and to improve combustion. The addition of oxygenates, such as methyl tertiarybutyl ether may be somewhere in the range of one-half to twenty percent by volume depending on the degree of non-attainment. In any event, these enhanced fuels will be more expensive. The possibility for substitution of a less costly non-attainment fuel arises, so close checks become important.

Responsibility lies with the refiner. Each refiner, and there are many, may employ what they believe to be a superior aromatic blend or a superior oxygenate, a superior mixture or optimum amounts in their gasolines to meet standards. Each refiner will need assurance that any condemned non-compliance fuel is the responsibility of another; in short, the refiner will need assurance that what is delivered to the consumer is what that refiner sold, and that if there is failure in compliance or other quality it is a matter of counterfeiting, tampering or cheating by another. The present invention addresses the need to effectively establish provenance not only for a large number of producers and refiners but for a large number of different hydrocarbons distributed by each producer source.

There are numerous other examples as to which provenance becomes important, from the standpoint of "not ours", the source or non-source of an oil spill, oil well leakage or unauthorized dumping; whether or not someone is surreptitiously diluting high octane with a lower octane; whether low grade motor oils are being substituted for a high grade label, or whether low quality lube fractions are employed to degrade a high priced lube of high quality, and sold at the higher price; whether low grade natural gas is being mixed with high grade methane or a natural gas otherwise degraded in terms of BTU's; whether waste dry cleaning fluid or some other cheap octane degrader is being dumped into a storage tank containing high octane gasoline, and so on.

Considering then the number of hydrocarbons (wellhead crude production and transportation of crudes, gasolines, diesel fuels, higher alkanes or alkenes for organic synthetics, lube fractions and natural gas, to list partially); and then to take into account the numerous producers and refiners, the various octanes or other grades, blends, and modifications, such as non-attainment grades, it can be visualized that tagging or labelling for provenance is of enormous magnitude.

Assume five producers, five hydrocarbons, three grades or quality ratings for each, and just three "non-attainment" modifications among the five. The possibilities are:

$$(5\times5\times3)+(5\times3) \text{ equal to } 90.$$

The tag or label disclosure according to U.S. Pat. No. 4,141,692 is consequently not the answer. While that disclosure does propose labeling to identify or distinguish sources, spills and co-mingling by employing tracer compounds susceptible to chromatographic-electron capture detection (CR/ECD), the concept there falls short of a binary system of detection featured under the present invention. Further, the compounds chosen for sensitivity according to U.S. Pat. No. 4,141,692 are a disparity of chloro-compounds which are not only corrosive upon combustion, but are environmentally unacceptable.

Also, if a different detectable label or tag is to be assigned to each hydrocarbon liquid, the result is; for 100 different liquids, one must rely on 100 different labels. This, of course, falls short of the plain fact that the number of hydrocarbon liquids will be much larger in the instance of supervising for or monitoring ten different producers or refiners.

Tracers and Markers

In an ever diversifying chemical, petroleum, and lubrication market, a need exists for uniquely identifying the various manufactured products. Labelling the vessels that contain the products is no longer sufficient. Numerous techniques have been used for marking liquids for the purpose of identification, sourcing and integrity. Typically hydrocarbon or aqueous based liquids can be uniquely marked by the addition of trace amounts of pure organic or inorganic compounds, respectively. The organic or inorganic marker system has to satisfy the following conditions:

A) The markers have to be detectable with confidence down to the part per million level, or below. In addition, the chemical and physical properties of the markers have to be unique, such that no component of the labeled bulk material can interfere with the analysis for the marker.

B) The detection method for the markers has to be fast (preferably less than 10–30 minutes per analysis). Detection methods that are accomplished in from about 10 seconds to 5 minutes would be optimal.

C) The analytical hardware to detect the markers should be minimal, readily available, and easily used.

D) The lifetime of the marker (or tracer compounds) has to exceed the lifetime of the labeled bulk material.

Ease of detection in the ppm (parts per million) range is the most crucial factor in selecting a potential marker system, and a variety of analytical methods should be available. The identification of the markers can take place in the bulk material itself or after a separation procedure. Separation methods that are easily implemented are gas chromatography, thin-layer and liquid chromatography. Each of these separation techniques entails specific detection methods. Gas chromatography (GC) can be coupled with:

1) Electron capture detection (ECD).
2) Flame ionization detection (FID).
3) Thermal conductivity detection (TCD).
4) Photo ionization detection (PID)
5) Thermionic specific detection (TSD)
6) Mass selective detection (MSD or MS)

High pressure liquid chromatography (HPLC) is one of the most effective form of liquid chromatography, and it can be coupled with the following detection methods:

1) Fluorescence detection.
2) Ultra violet (UV) absorption detection.
3) Refractive index (RI) detection.
4) Cyclic voltammetery (CV) electrochemical detection.

Analytical methods that satisfy the sensitivity condition demanded under A can be accomplished by the earlier described combination of gas chromatography and electron capture detection. An excellent alternative method for marker identification and detection is the combination of high pressure liquid chromatography and fluorescence detection.

Another technique would consist of sample preparation, thin-layer chromatography, U.V. excitation and then emission (preferably at U.V. or visible wavelength) visualization.

Summary of the Binary Counting System

In accordance with the present invention the labeling fluorescent compounds, to establish for family members, are arranged in a base 2 (binary) or higher matrix system $M^{n-1}$ where n is the number of labeling compounds and M is an independent variable, such as concentration. M relates to the number of possible values the independent variable can assume for a particular system. For example, when the variable is concentration and the system is base 2 (binary), then M has 2 possible values: 0 and 1. When the number is 0, the label is absent. When the number is 1, the label is present at a concentration high enough to be detected by the chosen fluorescent analytical method.

| Number of Unique Labeling Compounds | Number of Codes (base 2) |
| --- | --- |
| n | $2^{n}-1$ |

Therefore, simply by employing 10 fluorescent compounds, the possible unique combinations of the ten that can be used to identify liquids is $1024 - 1 = 1023$, which indeed is close to reality, because the invention first of all addresses the reality of the number of domestic producers and refiners who are or will be concerned. Under the binary system, there is room for the practice to be extended to many, many non-domestic producers and refiners as well.

Thus, to extend, if $n=15$, the possibilities are $32,768 - 1 = 32,767$. It therefore becomes possible to meet the needs of many producers and refiners throughout the world, or many different levels in the entire distribution system.

In addition, with precise application of a fluorescent labeling package and precise fluorescent analysis of the fluorophoric labeled liquid, dilutions of the liquid can be detected. All fluorophore packages would be dosed so that, upon analysis, the labels would produce a known theoretical response. Any response less than the expected value would indicate the liquid was diluted or otherwise modified.

The exact dosage of a fluorescent tracer code to an organic liquid A makes it also possible to trace and quantify liquid A once it has been mixed and diluted with a second organic liquid B. To be able to quantify the exact percentage of liquid A in liquid B, it is necessary to know the initial fluorescent itensity of the tracer code in pure liquid A and to have applied a fluorescent tracer package whose fluorescent emissivity is linear with respect to the concentration of the tracer dyes in the liquid. If no linear relationship exists between dye concentration and fluorescent emission a calibration curve can be produced to correlate fluorescence to concentration. Once these prerequisites have been fulfilled a hydrocarbon A containing a tracer can be quantified and traced after it has been mixed with a second hydrocarbon based liquid B.

Our invention is further related to the use of specific fluorophore compounds, and their homologs, to provide appropriately sensitive tracers to hydrocarbons for use in the labeling package of this invention.

PURPOSE OF OUR INVENTION

Four goals are defined for this invention.
1. Find a fluorescent dye that can be used as a tracing compound for many families of hydrocarbon liquids.
2. Synthesize a series of dye homologs that can be used in a binary counting system.
3. Develop a qualitive field method for identifying the dye code in gasoline, or other hydrocarbon liquids.
4. Develop a quantitative laboratory method for identifying the dye code in gasoline.

The Invention

Although many fluorophores were available, the N-substituted or N,N'-disubstituted 4-amino-1, 8-naphthalimides homolog series has been chosen for a tracer fluorophore package. Derivatization of the 4-amino-1,8-naphthalimide core fluorophore is available. The spectral and physical properties of this base fluorophore, and its homologs, are compatible with the proposed application as tracers for hydrocarbon liquids.

The fluorometric characteristics are outstanding:
lambda ex = 450 nm (blue/green)
lambda em = 550 nm (green/yellow)
Molar absorptivity = $1.40 \times 10^4$ L mole$^{-1}$ cm$^{-1}$

The Fluorophore Homologs

Preferably the fluorophore labeling compounds are homologs. Homologs are defined here as a series of chemical compounds which all contain the same molecular core and differ only by a substituent or substituents which are attached to the core molecule. The substituent, for example an alkyl radical, may be bound directly to the core through a carbon-carbon bond by a process of alkylation, acylation or nucleophilic substitution or be bound through a heteroatom such as oxygen, nitrogen, sulfur, or phosphorus. Functional groups, such as acetals and ketals, amides, amines, azos, carbamates, carbonates, carboxylic esters, disulfides, ethers, hydrazines, hydrazones, imides, imines, phosphonates, phosphates, sulfides, sulfonamides, sulfonic acid esters, ureas and others are appropriate for attaching substituents to a core molecule. The substituents can be anything that will alter the physical or chemical properties of the core molecule in a unique way so that all of the homologs will have a slightly different property that will allow them to be separated from each other by a separation technique, such as thin-layer or gas or liquid column chromatography. The substituents should not significantly alter the fluorescent properties of the core segment that allow it to be observed at low concentrations. For example, if a label is to be observed by a fluorescence detector attached to an HPLC (high pressure liquid chromatograph) separation system, the substituents on the core molecule should not cause significant variations in the emission characteristics of the series. Although unrelated labeling molecules can be used, a series of homologs is preferred over a series of unrelated materials.

First, from a manufacturing standpoint, it is far easier to produce a series of related homolog compounds than a series of unrelated ones. For homologs, the core substance can be purchased or manufactured, then derivatized, preferably in a single step. A complete series of labeling molecules can be made simply by attaching a series of alkyl radicals of varying sizes to the core molecule through an ester, amide, ether, amine or other easily formed linkage. On the other hand, each unique and unrelated labeling molecule would have to be manufactured by a costly multi-step synthesis.

Homologs are preferred because the physical and chemical properties of each label can be made to be very similar. This is important because it greatly simplifies the analytical procedure when the labeling molecules come out of the separation system sequentially and in close proximity to each other as opposed to at widely varying times which may occur with unrelated labeling molecules. Having the labeling molecules detected sequentially and in close proximity aids in the visualization of the binary code and more readily lends itself to full automation of the detection and data processing aspects of the system.

Homologs with similar physical and chemical properties are also more easily separated as a whole unit from the liquid they label. Under many circumstances, the liquid will contain unrelated substances that interfere with detection and the labels must be separated from the liquid before passing through the detector. It would be very difficult to guarantee that tracer molecules with widely varying properties could all be separated from the liquid by a single technique. Finally, the criteria for a labeling molecule to be compatible with the organic liquid to which it is added, and compatible with the application for which the liquid is intended can be very severe. It is very difficult to identify a series of unrelated molecules that meet all of the separability, detectability, and compatibility requirements for a given application. Since homologs have similar physical and chemical properties, these considerations are greatly simplified.

The Preferred Homologs

The 3-methoxypropyl, 3-ethoxypropyl, 3-isopropxypropyl, 3-n-butoxypropyl, methyl, ethyl, propyl, butyl, iso-butyl, pentyl, hexyl, octyl, nonyl, decyl, decylhexyl, octyl-butyl, butyl-ethyl and proypl-ethyl N,N' derivatives of 4-amino-1,8-napthalimide were synthesized as well as the N,N,N'-tributyl-4-amino-1,8-naphthalimide and 4-dibutylamino-1, 8-napthalimide dye. Ten of these dyes are suitable for producing a ten digit binary code that can be detected qualitatively in a field method by thin layer chromatography. In addition, any code produced by a combination of ten homologous dyes can be identified qualitatively and quantitatively in a laboratory procedure comprised of high pressure liquid chromatography and fluorescence detection. It is especially pertinent to note that any gasoline derived fluorophores are removed during chromatography and that detection of the naphthalimide tracers is possible well below the 0.1 ppm level.

Although it is preferred that a reasonable number of mono, di or trisubstituted naphthalimides be used, it is feasible, and within the scope of our invention, to use any substitution on the base fluorophore including, but not limited to, $C_1$-$C_{20}$ linear and branched alkyl groups, and as well as N,N' mono, di or trisubstituted ethoxylate, propoxylates, or mixtures thereof, or any cyclic, aromatic, alkaryl or aralkyl substituents on the naphthalimide base fluorophore.

Synthesis of Nitrogen Alkylated 4-Amino-1, 8-naphtalimides

A typical procedure for the synthesis of the homo diakyl 4-amino-1, 8-naphthalimides is given below:

To 120 gram of isopropanol in a 500 ml pressure reactor 0.1 mole of 4-chloro-1,8-naphthalic anhydride (technical grade), 1 mmole of copper powder and 0.4 mole of a primary amine were added. The vessel was sealed and under constant stirring brought to a temperature of 130° C. for 20 hours. Next the reaction mixture was cooled down to 25° C., and the vessel pressure was equalized to atmospheric pressure. To the reaction mixture 120 gram of toluene was added and the resulting solution was extracted three times with 100 grams of aqueous, saturated $NaHCO_3$. The final product mixture contained approximately 0.07 mol of the desired dye, 0.2 mole of the amine and 170 gram of an isopropanol-toluene mixture.

Above procedure was used to produce below compounds:
1) N-Ethyl-4(aminoethyl)-1,8-naphthalimide
2) N-n-Propyl-4(amino-n-propyl)-1,8-naphthalimide
3) N-n-Butyl-4(amino-n-butyl)1,8-naphthalimide
4) N-n-Pentyl-4(amino-n-pentyl)-1,8-naphthalimide
5) N-n-Hexyl-4(amino-n-hexyl)-1,8-naphthalimide
6) N-n-Octyl-4(amino-n-octyl)-1,8-naphthalimide
7) N-n-Decyl-4(amino-n-decyl)-1,8-naphthalimide
8) N-iso-Butyl-4(amino-iso-butyl)-1,8-naphthalimide A typical procedure for the synthesis of the homo alkoxyalkyl 4-amino-1,8-naphthalimides is given below:

To 120 gram of an alcohol, being the equivalent to the alkoxy group in the used alkoxy alkylamine, in a 500 ml pressure reactor 0.1 mole of 4-chloro-1,8-naphthalic anhydride (technical grade), 1 mole of copper powder and 0.4 mole of a primary alkylalkoxy amine were added. The vessel was sealed and under constant stirring brought to a temperature of 130° C. for 20 hours. Next the reaction mixture was cooled down to 25° C., and the vessel pressure was equalized to atmospheric pressure. To the reaction mixture 120 gram of toluene was added and the resulting solution was extracted three times with 100 grams of aqueous, saturated $NaHCO_3$. The final product mixture contained approximately 0.07 mol of the desired dye, 0.2 mole of the alkylalkoxy amine and 170 gram of an alcohol-toluene mixture.

Above procedure was used to produce below compounds:
1) N-(3-Methoxypropyl)-4-amino-(3-methoxypropyl)-1,8-naphthalimide; solvent: methanol
2) N-(3-Ethoxypropyl)-4-amino-(3-ethoxypropyl)-1,8-napthalimide; solvent: ethanol
3) N-(3-Isopropoxypropyl)-4-amino-(3-isopropoxypropyl)-1,8-naphthalimide; solvent: isopropanol 4) N-(3-n-Butoxypropyl)-4-amino-(3-n-butoxypropyl)-1,8-naphthalimide; solvent: n-butanol A typical procedure for the synthesis of the hetero dialkyl 4-amino-1,8-napthalimides is given below:

To 400 gram of ethanol in a 1L round bottom flask 0.2 mole of 4-chloro-1,8-naphthalic anhydride (technical grade) and 0.22 mole of a primary amine were added. The flask content was stirred and brought to a temperature of 45° C. for 8 hours. The reaction mixture was cooled down to 25° C., and all volatiles were removed to produce the solid N-alkyl-4-chloro-1,8-naphthalimide.

Next, to 80 gram of isopropanol in a 500 ml pressure reactor 0.05 mole N-alkyl-4-chloro-1, 8-naphthalimide (technical grade), 1 mmole of copper powder and 0.15 mole of a primary amine are added. The vessel was sealed and under constant stirring brought to a temperature of 130° C. for 20 hours. Next the reaction mixture was cooled down to 25° C., and the vessel pressure was equalized to atmospheric pressure. To the reaction mixture 120 gram of toluene was added, and the resulting solution was extracted three times with 100 grams of aqueous, saturated NaHCO$_3$. The final product mixture contained approximately 0.04 mole of the desired dye, 0.11 mole of the amine and 150 gram of an isopropanol-toluene mixture.

Above procedure was used to produce below compounds:
1) N-n-Butyl-4(aminoethyl)-1,8-naphthalimide
2) N-n-Propyl-4(aminoethyl)-1,8-naphthalimide

RESULTS AND DISCUSSION

A. N,N'-Dialkyl-4-amino-1,8-naphthalimides as Tracers

Of the many fluorescent molecules that do exist, only a very few might be usable as tracers for a hydrocarbon liquid, especially gasoline. The carbostyryls and coumarins are unsuitable due to their excitation and emission spectra in the region below 500 nm. The aromatic hydrocarbon components of gasoline can interfere with the detection of these types of dyes. The rhodamines and oxazines have excitation and emission spectra above 500 nm, but these fluorophores are used mostly in their salt form (chlorides, iodides, perchlorates). Fortunately, the N,N'-dialkyl-4-amino-1,8-naphthalimides are an all organic dye with an acceptable excitation and emission spectrum.

| Comparison of Excitation and Emission Wavelength of Fluorophores Considered and Gasoline | | |
|---|---|---|
| Type of Core Fluorophore | Lambda Excitation | Emission |
| Carbostyryls | 350–360 | 420–440 |
| Coumarins | 370–430 | 440–530 |
| Gasoline | 350–460 | 450–550 |
| 4-Amino-1,8-naphthalimides | 440 | 550 |
| Rhodamines | 510–680 | 530–800 |
| Oxazines | 600–670 | 630–810 |

Once the decision was made to use 4-amino-1,8 naphthalimides as tracers for hydrocarbons and especially for gasoline, the 20 compounds listed below were considered.
1. N-Methyl-4(aminomethyl)-1,8-naphthalimide
2. N-Ethyl-4(aminoethyl)-1,8-naphthalimide
3. N-n-Propyl-4(amino-n-propyl)-1,8-naphthalimide
4. N-n-Butyl-4(amino-n-butyl)-1,8-naphthalimide
5. N-n-Pentyl-4(amino-n-pentyl)-1,8-naphthalimide
6. N-n-Hexyl-4(amino-n-hexyl)-1,8-naphthalimide
7. N-n-Octyl-4(amino-n-octyl)-1,8-naphthalimide
8. N-n-Decyl-4(amino-n-decyl)-1,8-naphthalimide
9. N-iso-Butyl-4(amino-iso-butyl)-1,8-naphthalimide
10. N-(3-Methoxypropyl)-4-amino-(3-methoxypropyl)-1,8-naphthalimide
11. N-(3-Ethoxypropyl)-4-amino-(3-ethoxypropyl)-1,8-naphthalimide
12. N-(3-Isopropoxypropyl)-4-amino-(3-isopropoxypropyl)-1,8-naphthalimide
13. N-(3-n-Butoxypropyl)-4-amino-(3-n-butoxypropyl)-1,8-naphthalimide
14. N-n-Propyl-4(aminoethyl)-1,8-naphthalimide
15. N-n-Butyl-4(aminoethyl)-1,8-naphthalimide
17. N-n-Octyl-4(amino-iso-butyl)-1,8-naphthalimide
18. N-n-Decyl-4(amino-n-hexyl)-1,8-naphthalimide
19. N-n-Butyl-4(amino-di-n-butyl)-1,8-naphthalimide
20. 4-(Amino-di-n-butyl)-1,8-naphthalimide Of these 20 naphthalimide dyes, the diethyl, dipropyl, dibutyl, dipentyl, dihexyl, dinonyl, di-3-methoxypropyl, di-3-ethoxypropyl, di-3-isopropoxypropyl, and di-3-n-butoxypropyl naphthalimide dye were chosen for the binary tracer system. The other dyes were excluded for various reasons.

However, while homologs are preferred for the aforementioned reasons, it is understood that there are cases where the use of unrelated molecules in a labeling system provides adequate results, and thus the digital coding system is not restricted to homologs.

Preferably the labeling compounds (solutes) are homologs. Ten homologs that provide $2^{10}-1$ unique labels (for example) are easier to manufacture than 1023 tracers which are not homologs, to say nothing of detection disparity. Further, both a chromatograph, or other separator, and a fluorescent analog detector would be easier to assemble and operate for detection of a series of homologs compared to labels of widely variant chemistry.

The advantage of homologs can be best explained in terms of liquid or thin-layer chromatography as the preferred technique for separation. In liquid chromatography the term "distribution coefficient" is often employed to characterize separation of a compound from the carrier traveling through the chromatograph column. Two different compounds will elute from the column at different times; they are distributed differently between the liquid carrier solvent (mobile phase) and the solid stationary phase when traveling through the column and this difference in distribution is what accounts for their eluting or leaving the column at different times.

The distribution difference tracer dyes is effected by (1) their affinity for the solid support; (2) their solubility in the mobil phase; (3) their polarity; (4) the manner or mode of packing the column (e.g. with silicagel, aluminium oxide); (5) diameter and length of the column; (6) the flow rate of the mobil phase.

It is, therefore, easier to operate a liquid chromatographic system for related compounds than unrelated compounds because the distribution, coefficients will have a predictable range. Similar characteristics of the other chromatographic techniques provide for similar advantages of the present fluorophore compounds and their homologs.

Thin Layer Chromatography Field Method For Identifying Fluorescent Tracer Codes in Gasoline The following method was developed to produce a dye enriched liquid sample that can be used for TLC separation to reveal the binary code in a gasoline sample spiked with naphthalimide tracers:

A sample of gasoline (200 mL) containing up to ten different N,N'-dialkyl-4-amino-1,8-naphthalimide tracer dyes, each at 0.05 ppm, is passed through a Waters Sep-Pak cartridge containing either 900 mg Florisil or 1850 mg Alumina A. All dyes are retained at the beginning of the packing material and form a visible green band.

The gasoline is washed off the Sep-Pak with 20 mL of heptane. A syringe filled with three mL of acetone is attached to the Sep-Pak opposite to the end that contains the dyes. Approximately the first one mL of acetone that passes through the Sep-Pak displaces all of the heptane and this eluant is discarded as long as it is water white. As soon as the eluant changes from water white to green, one additional mL of acetone is passed through the Sep-Pak and this eluant is collected. This one mL contains all the tracer dyes that were present in the gasoline at a hundred fold concentration. The individual dye concentration has been increased from 0.05 ppm to 10 ppm. A 20 micro liter sample of the concentrate is applied to a TLC plate 1 cm from both edges (silica gel, 2-23 micro meter mean particle size, 60 angstrom mean pore diameter, plate size 3×24 cm), forming a spot with a diameter no larger than one eighth of an inch. A 20 micro liter sample of a standard solution that contains all tracer dyes at a concentration of 10 ppm is applied next to the spot that was formed by the extract. Both spots are developed with a toluene/acetone, 9/1 mixture. The solvent shall travel at least 20 cm to obtain a good separation of all individual tracer dyes.

Comparison of the standard and the extract TLC trace reveals the binary code of the gasoline through the presence or absence of the individual dyes. The code on the TLC plate is read from left to right, having on the right side the original sample spot and on the left side the solvent front. If the extract trace shows a colored spot directly above a standard trace spot, it is read as one. If no dye can be seen directly above a dye spot for the standard, it is read as zero.

High Pressure Liquid Chromatography Laboratory Method for Identifying Fluorescent Tracer Codes in Gasoline No sample preparation is necessary for identifying the tracer codes in gasoline or toluene by high pressure liquid chromatography. The instrumental setup consists of an auto sampler, a HPLC pump, a HPLC column and a fluorescent detector as well as a data acquisition system. The general instrumental parameters are:

Autosampler:
Injection Loop Size (uL): 25 (50, 100)
Pump: Spectro Physics, SP 8810 precision isocratic pump
Flowrate (mL/min): 0.5 to 1.5
Mobile Phase: 0 to 15% Acetone, rest toluene (or other solvent mixtures)
Run Time (min): 5 to 20
Temperature: ambient
Column: Silica gel
Particle Size (um): 5
Column Length (mm): 250
Column I.D. (mm): 4.6
Detector: Fluorescence HPLC Monitor
Excitation Wavelength (nm): 420 to 450
Observed Emission Wavelength: 480 to 550

Results—Thin Layer Chromatography (TLC) for Identifying Fluorescent Tracer Codes in Gasoline Each dye that represents a single digit in the binary tracing code has been dosed at 0.05 ppm in the gasoline. Using a ten digit identification code, the total dosage of fluorescent dyes in the gasoline can vary between 0.05 ppm and 0.5 ppm. At this concentration, the dyes impart no visible color on the marked fuel. Unfortunately, spotting a 0.05 to 0.5 ppm solution of a N,N'-dialkyl-4-amino-1,8-naphthalimide on a TLC plate produces no visible color response. Therefore, the liquid spotted on the TLC plate has to be enriched in its dye content as described above.

The dinonyl, dihexyl, dipentyl, dibutyl, dipropyl and diethyl, 3-di-n-butoxypropyl, 3-di-iso-propoxypropyl, 3-di-ethoxypropyl, and 3-di-methoxypropyl derivatives were selected for the ten digit binary coding system. Each of these dyes has a unique $R_f$ and produces a distinct yellow-green spot on a silica gel plate under above described conditions. First the TLC behavior of the individual dyes is demonstrated and then four binary sample codes are shown on the next page.

| all dyes | individual dyes | | | | | | | | | dye* giving the response | binary value | decimal value |
|---|---|---|---|---|---|---|---|---|---|---|---|---|
| | Top solvent front | | | | | | | | | | | |
| O | | | | | | | | | | O Nonyl | 1000000000 | 512 |
| O | | | | | | | | | | O Hexyl | 0100000000 | 256 |
| O | | | | | | | | O | | Pentyl | 0010000000 | 128 |
| O | | | | | | | O | | | Butyl | 0001000000 | 64 |
| O | | | | | | O | | | | Propyl | 0000100000 | 32 |
| O | | | | | O | | | | | 3-n-Butoxypropyl | 0000010000 | 16 |
| O | | | | O | | | | | | Ethyl | 0000001000 | 8 |
| O | | | O | | | | | | | 3-iso-Propoxypropyl | 0000000100 | 4 |
| O | | O | | | | | | | | 3-Ethoxypropyl | 0000000010 | 2 |
| O | O | | | | | | | | | 3-Methoxypropyl | 0000000001 | 1 |
| x | x | x | x | x | x | x | x | x | x | Dye origin on the TLC plate | | |

\* = N-Alkyl-4(aminoalkyl)-1,8-naphthalimide
O = visible fluorescent green spot from dye These ten distinguishable fluorescent spots can be translated to a ten digit binary number where the absence of the dye counts as a zero and the presence counts as a one. Shown below is a scheme that exemplifies the TLC method for the binary numbers 101100011 (354 decimal), 1000011010 (538 decimal), and 100111 (39 decimal).

| TLC Response of Selected Tracer Codes | | | | |
|---|---|---|---|---|
| decimal number | standard examples of individual tracer codes | | | |
| binary number | 1023 1111111111 | 538 1000011010 | 354 0101100010 | 39 0000100111 |
| | O | O | — | — |
| | O | — | O | — |
| | O | — | — | — |
| | O | — | O | — |
| | O | — | O | O |
| | O | O | — | — |
| | O | O | — | — |
| | O | — | — | O |
| | O | O | O | O |
| | O | — | — | O |
| Dye spot on TLC | X | X | X | X |

O = visible fluorescent green spot from dye

Results - Digital Dye Codes

Of the synthesized fluorescent dyes, distinguishable by HPLC, the diethyl, dipropyl, dibutyl, dipentyl, dihexyl, dinonyl, di-3-n-butoxypropyl, di-3-isopropoxypropyl, di-3-ethoxy propyl, and di-3-methoxy propyl derivative were used to produce a ten digit binary number. Each dye used was dosed at 0.1 ppm. Test codes were produced to confirm that the individual dyes do not overlap in a chromatogram. The binary code of the gasoline is produced through the presence or absence of the individual dyes at their specific retention times. The code is read from the HPLC recorder trace from left to right, having on the left side the compounds with the shortest retention time and on the right side the compounds with the longest retention time. If the HPLC trace shows at a compound specific retention time a response below a predetermined level, a zero is read for the binary code. If a response above a predetermined level is observed, a one is read for the binary code. Shown below is a scheme that exemplifies the HPLC method for producing binary numbers.

| HPLC Response of Selected Tracer Codes | | | | |
|---|---|---|---|---|
| decimal number binary number | 1023 1111111111 | 538 1000011010 | 354 0101100010 | 39 0000100111 |
| HPLC retention times for | | | | |
| Nonyl 3.70 | X | X | — | — |
| Hexyl 3.95 | X | — | X | — |
| Pentyl 4.27 | X | — | — | — |
| Butyl 4.81 | X | — | X | — |
| Propyl 5.76 | X | — | X | X |
| Butoxypropyl 7.16 | X | X | — | — |
| Ethyl 7.42 | X | X | — | — |
| Propoxypropyl 10.69 | X | — | — | X |
| Ethoxypropyl 13.50 | X | X | X | X |
| Methoxypropyl 19.79 | X | — | — | X |

X = dye present
— = dye absent

The chromatograms shows that it is possible to form binary codes with the available ten dyes. The response peaks for the individual dye are separated at the baseline and each peak can be integrated for quantization.

Gasoline Compatibility Results

Having established that a binary code can be imparted on a hydrocarbon liquid by addition of selected dyes, the compatibility of the dyes with the gasoline had to be studied. Ten different gasolines were selected and spiked with the dyes each at 0.1 ppm. The gasolines chosen are listed below.

| Gasolines Used for Compatibility Tests | | | |
|---|---|---|---|
| Gasoline Brand | Refinery Location | Gasoline Type | Date Sampled |
| A | California | not specified | 4-22-91 |
| B | | not specified | 1-29-91 |
| C | Louisiana | Regular Unleaded | 5-3-91 |
| D | Texas | Premium Unleaded | 2-22-91 |
| E | Wyoming | Premium Unleaded | 5-28-91 |
| F | Wyoming | Regular Unleaded | 5-28-91 |
| G | Pennsylvania | Premium Unleaded | 5-23-91 |
| H | Utah | Premium Unleaded | 5-23-91 |
| I | Utah | Regular Unleaded | 5-23-91 |

The dyes could be clearly observed in all gasolines at a level of 0.1 ppm. In no case did any residual fluorescence from the gasoline interfere with the responses produced by the dialkyl-4-amino-1,8-naphthalimides.

Having described my invention, I claim:

1. An identification system for identification of a family of organic hydrocarbon fluids comprising the following method steps:

a) adding at least one of (n) fluorescent fluorophore labeling compounds to a hydrocarbon fluid to produce a mixture of the labeling compound with the hydrocarbon fluid representing the source point of the hydrocarbon fluid and labeling compound, the source point being at a different location from the destination point to which the mixture is transported, wherein the labeling compounds are N-substituted or n,N'-disubstituted 4-amino-1,8 naphthalimide homologs;

b) obtaining at a destination point a sample of a mixture of hydrocarbon fluid to which the (n) labeling compounds have been added according to step a;

c) passing the labeled hydrocarbon fluid through a predetermined separation device capable of separating the mixtures of hydrocarbon fluid from the labeling compounds based on the individual characteristics of the labeling compounds and detecting the presence or absence of the (n) number of fluorescent labeling compounds contained in the hydrocarbon fluid according to their separation and fluorescent characteristics; and d) comparing the separation and fluorescence characteristics of the (n) number of fluorescent labeling compounds to known separation and fluorescent characteristics of the (n) fluorescent labeling compounds which facilitate the identification of the fluorescent labeling compounds in the hydrocarbon mixture, wherein a binary notation is employed such that the absence of detection of a specific fluorescent fluorophore labeling compound is represented by the value (0) and the presence of detection of a specific fluorescent fluorophore labeling compound is represented by (1), thus permitting the n number of labeling compounds to produce $2^n - 1$ possible unique codes and wherein each unique code is correlated to the labeling of the organic hydrocarbon fluid that is representative of the organic hydrocarbon fluid which was labeled at its source, and thereby identifying the labeled organic hydrocarbon fluid.

2. The system according to claim 1 where the fluorescent emissions are detected by fluorescent detection and analysis resulting from the labeling compounds absorbing then emitting light at a different wavelength.

3. The system of claim 1 wherein the N,N' disubstituted-4-amino-1,8-naphthalimides are N,N' dialkyl substituted-4-amino-1,8-naphthalimides and the dialkyl substituents contain from 1 to about 20 carbon atoms and are linear, branched, or mixtures thereof.

4. The system of claim 1 wherein the fluorescent fluorophore labeling compounds include N,N'-di(alkoxyalkyl) substituted 4-amino-1,8-naphthalimide compounds where the alkoxyalkyl substituents [$H_3C$-$(CH_2)_n$-O-$(CH_2)_n$-] are selected from the group consisting of 3-methoxypropylamine, 3-ethoxypropylamine, 3-iso-propoxypropylamine, 3-n-butoxypropylamine and the equivalent branched groups thereof.

5. The system of claim 1 wherein the substituents are alkoxyalkyl substituents selected from the general formula $H_3C$-$(CH_2)_2$-[O-$(CH_2)_n$]$_m$ or wherein the substituents are alkyl substituents selected from the group consisting of $C_1$-$C_{20}$ linear and branched alkyl groups, and further wherein the fluorophore adsorbent is selected from of the group consisting of silica gel, alumina, and aluminosilicates, and further wherein the polar organic solvent is selected from the group consisting of $C_1$-$C_6$ alcohols, $C_3$-$C_6$ ketones, $C_2$-$C_6$ amides, dimethyl sulfoxide, dimethyl formamide, and $C_1$-$C_3$ nitriles; and further wherein the presence of said fluorophore compound and its homologs is determined by sampling a small volume of polar solvent-fluorophore and placing said sample on a thin-layer chromatographic plate containing a thin-layer of adsorbent selected from the group consisting of alumina, silica, and aluminosilicates, and eluting said thin layer plate with a developer solvent, drying, and exposing same to a light source emitting a wavelength, which excites a fluorescent emission which allows determination of a code and thereby providing the identity of said organic fluid.

6. The system of claim 1 wherein the labeling compound is n-N'-disubstituted 4-amino-1,8-naphthalamide and the homologs are selected from the group consisting of:

N-Methyl-4(aminomethyl)-1,8-naphthalimide,
N-Ethyl-4(aminoethyl)-1,8-naphthalimide,
N-n-Propyl-4(amino-n-propyl)-1,8-naphthalimide,
N-n-Butyl-4(amino-n-butyl)-1,8-naphthalimide,
N-n-Pentyl-4(amino-n-pentyl)-1,8-naphthalimide,
N-n-Hexyl-4(amino-n-hexyl)-1,8-naphthalimide,
N-n-Heptyl-4(amino-n-heptyl)-1,8-naphthalimide,
N-n-Octyl-4(amino-n-octyl)-1,8-naphthalimide,
N-n-Nonyl-4(amino-n-nonyl)-1,8-naphthalimide,
N-n-Decyl-4(amino-n-decyl)-1,8-naphthalimide,
N-iso-Butyl-4(amino-iso-butyl)-1,8-naphthalimide,
N-(3-Methoxypropyl)-4-amino-(3-methoxypropyl)-1,8-naphthalimide; solvent: methanol,
N-(3-Ethoxypropyl)-4-amino-(3-ethoxypropyl)-1,8-naphthalimide; solvent: ethanol,
N-(3-isopropoxypropyl)-4-amino-(3-isopropoxypropyl) 1,8-naphthalimide; solvent: isopropanol,
N-(3-n-Butoxypropyl)-4-amino-(3-n-butoxypropyl)-1,8-naphthalimide; solvent: n-butanol,
N-n-Butyl-4(aminoethyl)-1,8-naphthalimide and
N-n-Propyl-4(aminoethyl)-1,8-naphthalimide.

7. The system of claim 6 wherein the parent compound is 4-amino-1,8-naphththalimide and the homologs also include assymetric N,N'-dialkyl substituted 4-amino-1,8-naphthalamide compounds where the alkyl substituents are selected from the group consisting of methyl, ethyl, propyl, butyl pentyl, hexyl, heptyl, octyl, nonyl, decyl alkyl groups, and the equivalent branched groups thereof.

8. The system of claim 1 wherein the organic hydrocarbon fluid is a petroleum based fluid selected from the group consisting of gasoline, diesel fuel, and lubricating oils, the fluorophore labeling compounds comprise n,N'-disubstituted homologs of 4-amino-1, 8-naphthalimide, and the preselected analysis method is as follows:

1) obtain from the source of origin a sample of organic fluid of a known volume, said volume being of sufficient size to permit the detection of the fluorophore labeling compounds;

2) Add said sample to an amount of solid adsorbent, said adsorbent having the capacity to adsorb thereon the fluorophore labeling compounds;

3) Wash said solid adsorbent with a pure hydrocarbon liquid capable of removing all organic hydrocarbon fluid therefrom while leaving said fluorophore labeling compounds adsorbed thereon;

4) Then, washing said solid adsorbent with a polar solvent capable of removing and eluting said fluorophore labeling compounds from said adsorbent, the volume of said polar solvent relative to the volume of said organic fluid sample being in a ratio of from about 1:1,000,0000 to about 1:100, thereby providing a polar solvent-fluorophore labeling compound sample; and 5) Determining the presence or absence of said fluorophore compound and up to said n number of homologs thereof, thereby revealing said code and identifying said organic fluid.

9. The process of claim 8 wherein the fluorophore adsorbent is contained within a high pressure liquid chromatographic column and the presence of the fluorophore is detected by fluorescent technique and compared to standard curves for the same fluorophore compound and its homologs used to form the selected permutations of labeling compounds.

10. The system according to claim 1 where the labeling compounds are selected so that, during the analysis of the separation profile, the detected specific said fluorescent labels in the fluid are correlated to a known standard of discrete predetermined separation distances d1 through dn which indicates the presence or absence of said (1 – n) fluorescent labels respectively.

11. The system according to claim 10 where the separation of the labeling compounds is done by thin layer chromatography (TLC) and the separated labeling compounds (1−n) are at distances d1 through dn which correlates to the known standards where the presence or absence of said (1−n) labeling compounds is indicated by the binary notation 1 or 0 respectively and thereby producing a binary number that is specific for the labeled hydrocarbon fluid.

* * * * *